United States Patent [19]
Jonese

[11] Patent Number: 5,443,161
[45] Date of Patent: Aug. 22, 1995

[54] DISPOSABLE BABY CHANGE KIT

[76] Inventor: David R. Jonese, P.O. Box 5, Arbovale, W. Va. 24915

[21] Appl. No.: 279,880

[22] Filed: Jul. 26, 1994

[51] Int. Cl.6 .......................................... B65D 30/22
[52] U.S. Cl. ................................. 206/581; 206/38; 206/278; 206/494
[58] Field of Search ............... 206/581, 204, 278, 38, 206/440, 37, 494; 383/121, 122, 207, 208

[56] References Cited

U.S. PATENT DOCUMENTS

| | | |
|---|---|---|
| 2,825,208 | 3/1958 | Anderson . |
| 3,121,452 | 2/1964 | Hyman ............................ 383/121 X |
| 3,608,566 | 11/1971 | Storandt . |
| 4,221,221 | 9/1980 | Ehrlich . |
| 4,685,559 | 8/1987 | Titus . |
| 4,702,378 | 10/1987 | Finkel et al. . |
| 4,738,678 | 4/1988 | Paulis . |
| 4,790,840 | 12/1988 | Cortina . |
| 4,886,150 | 12/1989 | Fitzsimmons . |
| 4,934,535 | 6/1990 | Muckenfuhs et al. ............... 206/494 |
| 4,938,608 | 7/1990 | Espinosa . |
| 4,961,522 | 10/1990 | Weber . |
| 4,966,286 | 10/1990 | Muckenfuhs .................... 206/440 X |
| 4,998,620 | 3/1991 | Taylor .................................. 206/440 |
| 5,062,557 | 11/1991 | Mabvi et al. . |
| 5,065,868 | 11/1991 | Cornelissen et al. ........... 206/440 X |
| 5,163,756 | 11/1992 | Riseman . |
| 5,261,531 | 11/1993 | Nieves . |
| 5,307,988 | 5/1994 | Focke et al. ..................... 206/494 X |

*Primary Examiner*—Jacob K. Ackun
*Attorney, Agent, or Firm*—Richard C. Litman

[57] ABSTRACT

The present invention relates to a disposable kit having a plurality of baby care supplies stored within a moisture impermeable enclosure. The kit includes supplies for two complete diaper changes, and it is easy to manufacture and extremely compact. A tear line, fabricated from a weakened portion within one of the enclosure walls, permits for easy access to the contents stored within the enclosure. These contents are two diapers, two moisture impermeable disposal bags, two wet wiping elements, baby powder, and baby cream. To provide the enclosure with a uniform and pliable surface, the two diapers are arranged to be substantially entirely in contact with opposing sides of the enclosure.

7 Claims, 4 Drawing Sheets

DISPOSABLE BABY CHANGE KIT

BACKGROUND OF THE INVENTION

1. FIELD OF THE INVENTION

The present invention relates to a compact and disposable kit containing a plurality of baby care supplies. Specifically, the present invention relates to an easily transportable kit wherein an easy to open and moisture impermeable enclosure stores the baby care supplies.

2. DESCRIPTION OF THE PRIOR ART

As numerous supplies are required for proper care of a baby, it is very difficult for one person to carry these supplies without inhibiting his or her ability to adequately attend to the baby. To remedy this problem, there have been many inventions concerned with devices that allow a plurality of baby supplies to be simultaneously and conveniently stored in a single, easy to carry apparatus.

The most common apparatus for carrying a plurality of baby supplies is a standard utility bag, variations of which can be seen in U.S. Pat. No. 2,825,208 issued to Daphene W. Anderson on Mar. 4, 1958, U.S. Pat. No. 4,685,559 issued to Hubert W. Titus on Aug. 11, 1987, U.S. Pat. No. 4,702,378 issued to Henry Finkel, et al. on Oct. 27, 1987, U.S. Pat. No. 4,886,150 issued to Julie-Anna Fitzsimmons on Dec. 12, 1989, U.S. Pat. No. 4,961,522 issued to Randi R. Weber on Oct. 9, 1990, and U.S. Pat. No. 5,062,557 issued to A. Pascal Mabvi, et al. on Nov. 5, 1991.

The Anderson patent relates to a handbag having a hinged cover and handles. The inside panel of this handbag includes a plurality of pouches, one of which is adapted to retain a refrigerant for cooling items stored within the remaining pouches.

The Titus patent discloses a diaper caddy for carrying disposable diapers and related infant supplies. Included in this invention is a sliding drawer and a pair of trays, all for storing various baby supplies. Also included in the invention is a plurality of compartments, specifically configured for accepting diapers. Each of these compartments have a dispensing slot through which the diapers are individually dispensed.

The invention illustrated in the Finkel patent is a single use disposable baby change kit fabricated from a thin plastic film having a leading section and a trailing section. The leading section is folded upon itself to form a pocket, and the trailing section is folded upon itself to form a pouch. A pair of plastic panels are secured to the trailing section to form a pair of opposing pockets. One of these pockets is for receiving a diaper, and the other pocket is utilized as a flap when sealing the contents of the kit within the plastic film.

The Fitzsimmons patent teaches a carrying device foldable into two configurations. In the first configuration, the device forms a central pocket for carrying and storing various baby supplies. At the bottom of this pocket is a water impermeable pad that is exposed only when the device is folded into the second configuration. This water impermeable pad is utilized as a surface upon which a baby can be changed.

The Weber patent shows a travel pack convertible to different carrying modes, and the Mabvi, et al. patent shows an infant care bag having a primary bag section and a removable auxiliary bag section. The primary bag section stores a variety of supplies, and it is usable as a booster chair for dining. The removable auxiliary section provides additional storage space and has a compartment for storing a baby change pad.

In addition to bags for carrying a plurality of baby supplies, it has been common to attach baby supplies directly to a diaper. This assures that necessary supplies do not get separated from the diaper, and it also minimizes the amount of items that must be carried when traveling with a baby. Patents illustrating diapers capable of storing supplies are U.S. Pat. No. 4,221,221 issued to Jimmie L. Ehrlich on Sep. 9, 1980, U.S. Pat. No. 4,738,678 issued to Robert A. Paulis on Apr. 19, 1988, and U.S. Pat. No. 4,790,840 issued to Cathy Cortina on Dec. 13, 1988.

The Ehrlich patent illustrates a utility diaper having a plurality of containers releasably connected thereto. These containers each form a sanitary compartment for the storage of baby care supplies.

The Paulis patent shows a diaper having an adhesive tab for securing the diaper in a folded position, and also for retaining a pre-moistened towelette to the surface of the diaper. When the tab is removed, the diaper unfolds, leaving the towelette ready for immediate use.

A towelette is also mounted to the diaper disclosed in the Cortina patent. This towelette is contained in a closed package mounted to the surface of the diaper, and a tear strip is utilized to separate the package from the diaper.

Patents relevant to, but not specifically designed for, the storage of baby items, are U.S. Pat. No. 3,608,566 issued to Duane L. Storandt on Sep. 28, 1971, U.S. Pat. No. 4,938,608 issued to Daniel Espinosa on Jul. 3, 1990, U.S. Pat. No. 5,163,756 issued to David A. Riseman on Nov. 17, 1992, and U.S. Pat. No. 5,261,531 issued to Felipe A. Nieves on Nov. 16, 1993.

The Storandt patent teaches an applicator package having an inner pouch of moisture absorptive material enclosed within an outer pouch. A tear string disposed around the perimeter of the outer pouch facilitates opening of the pouch.

The Espinosa patent illustrates a plurality of thin plastic bags arranged in a series, and wrapped around a dispensing roll. At the junction of adjacent bags, there is a perforation for facilitating both separation of the bags and opening of the removed bag.

The Riseman patent teaches a flexible bag having a removable section capable of receiving items to be stored or carried. A perforated attachment between the removable section and the bag allows for easy separation of the component parts.

The Nieves patent shows a feminine hygiene package for cleansing the body after discharge of body fluids. A dry wipe, an enclosed wet wipe, and a sanitary napkin are enclosed in an encasing during storage. The encasing has a length and width not exceeding 20 cm and 10 cm, respectively, and it is usable for post use disposal of the wipes and the sanitary napkin.

None of the above inventions and patents, taken either singly or in combination, is seen to describe the instant invention as claimed.

SUMMARY OF THE INVENTION

The present invention relates to a compact and disposable kit having a plurality of baby care supplies stored within a moisture impermeable enclosure. A tear line, fabricated from a weakened portion within one of the enclosure walls, permits easy access to the contents stored within the enclosure. These contents, which include baby care items sufficient for two diaper changings, are two diapers, two moisture impermeable disposal bags, two wet wiping elements, baby powder, and baby cream. To provide the enclosure with a uniform and pliable surface, the two diapers are arranged to be substantially entirely in contact with opposing sides of the enclosure. This uniform and pliable surface facilitates carrying and storage of the enclosure, and it also provides a surface capable of receiving printed matter and the like. After the enclosure is opened and some of the supplies have been utilized, the soiled supplies are placed within one of the moisture impermeable disposal bags, and the remaining supplies are retained within the enclosure for future use.

Accordingly, it is a principal object of the invention to provide a novel kit usable for two diaper changings.

It is another object of the invention to provide a novel kit having a plurality of baby care supplies stored within a moisture impermeable and extremely compact enclosure.

It is a further object of the invention to provide a novel kit having a moisture impermeable enclosure that may be readily opened for accessing the supplies stored therein.

Still another object of the invention is to provide a novel kit having a moisture impermeable enclosure with a uniform and pliable surface.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
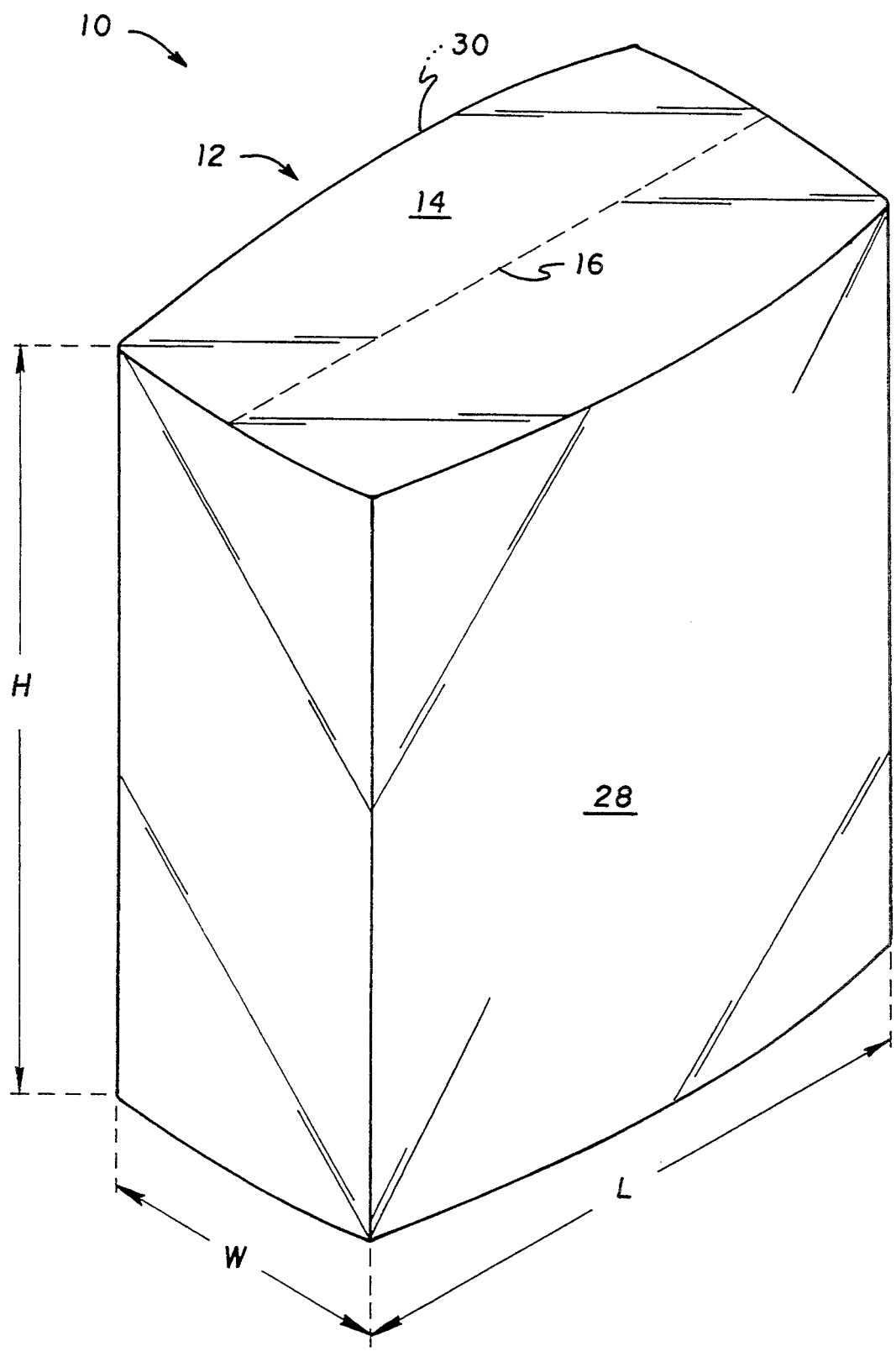
FIG. 1 is a front perspective view of the baby change kit of the invention.

Referring to FIG. 1, the present invention is a baby change kit 10 having an enclosure 12, housing a plurality of baby care supplies. This enclosure 12 completely encircles the items stored therein, and it is fabricated from a thin, strong, flexible, moisture impermeable material, such as 2 millimeter thick polypropylene based plastic. Enclosure 12 is very compact and may be easily carried in a pocket, purse, or similar article. In one preferred embodiment, the approximate dimensions of the height H, length L, and width W of the enclosure are 4.5 inches, 4 inches, and 2 inches, respectively.

The top surface 14 of this enclosure includes a tear line 16 permitting easy opening of enclosure 12. In the preferred embodiment of the invention, tear line 16 is formed as a weakened portion of the polypropylene material. When this weakened portion is pressed by a user's fingers, top surface 14 is severed along tear line 16, creating an opening 18 (shown in FIG. 2) for accessing the baby care supplies. This type of tear line 16 is easily manufactured and severed, but prior to being severed, it is completely moisture impermeable. Other acceptable, but not preferred, configurations of tear line 16 include a standard releasing enclosure formed from two opposing and interlocking surfaces, or a release strip with a section of adhesive attached to top surface 14 to cover an open slot, by way of example.

Figure 2:
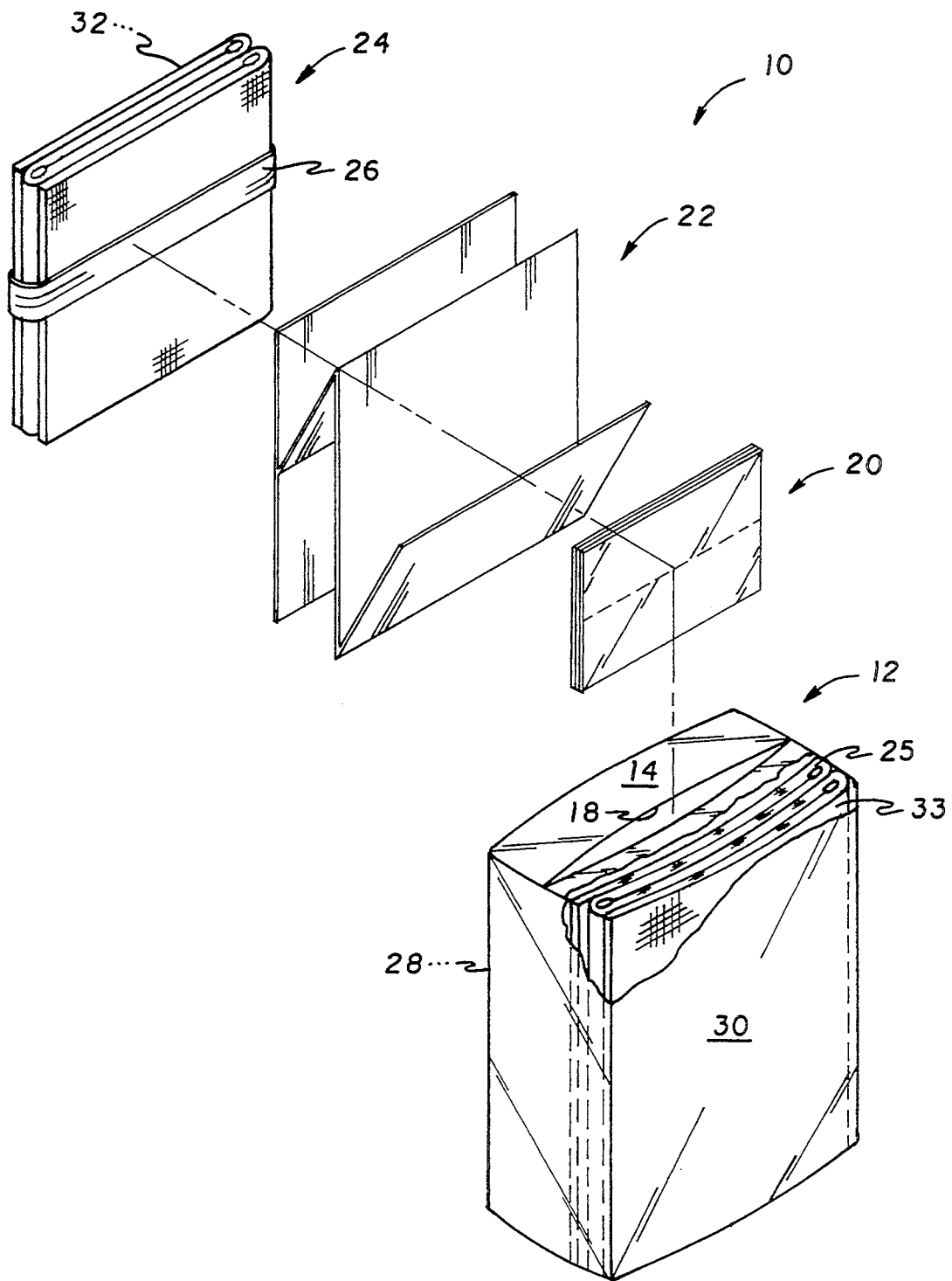
FIG. 2 is a partially exploded, front perspective view of the baby change kit shown in FIG. 1.

In FIG. 2, shown is a package of baby wipes 20, a disposal bag 22, and a diaper 24 maintained in a folded position by a tie strap 26. Positioned within enclosure 12 are diaper 25 and other supplies that may either be removed through opening 18 or retained within enclosure 12 for future utilization.

Figure 3:
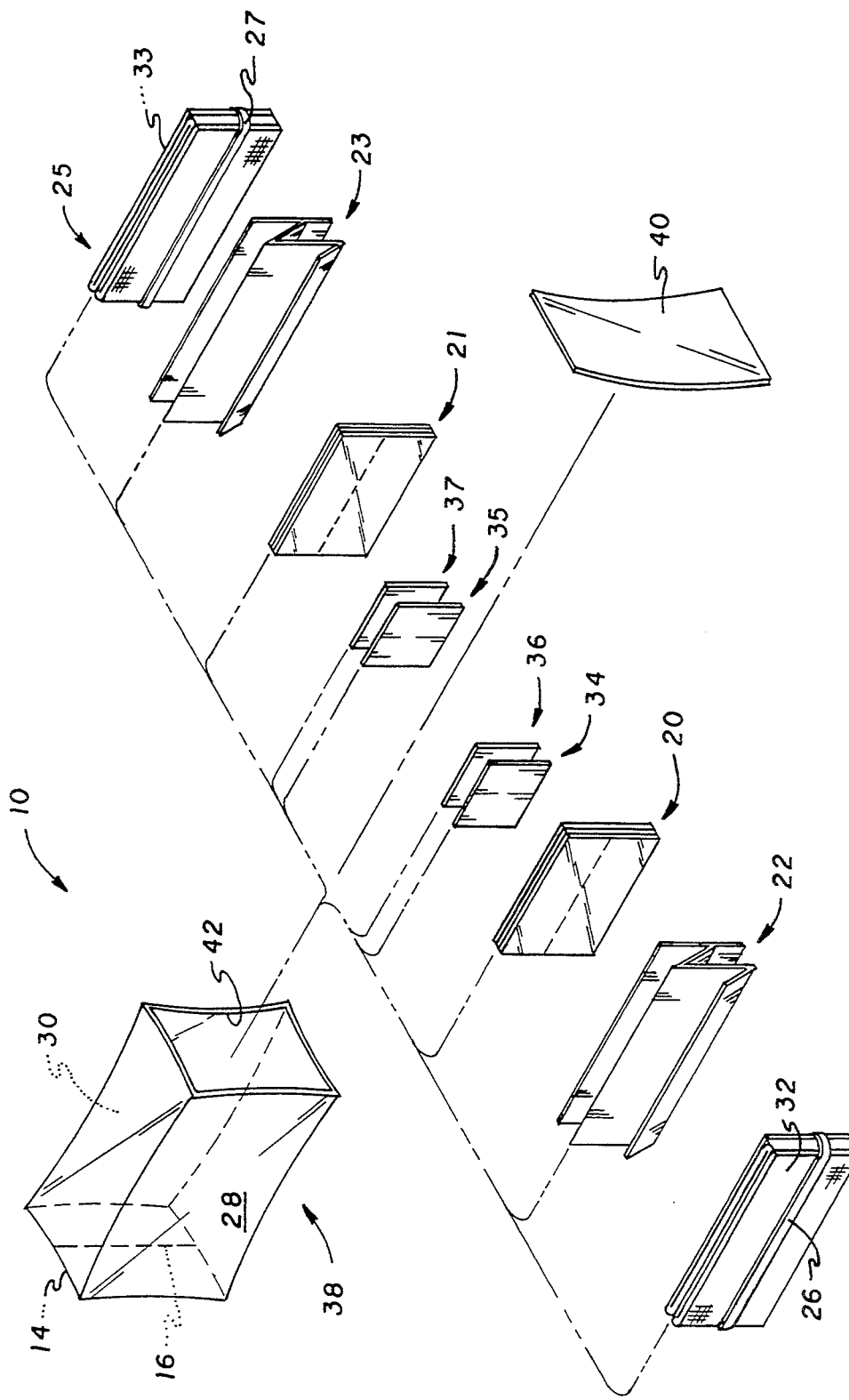
FIG. 3 is an exploded, rear perspective view of the baby change kit shown in FIG. 1.
Figure 4:
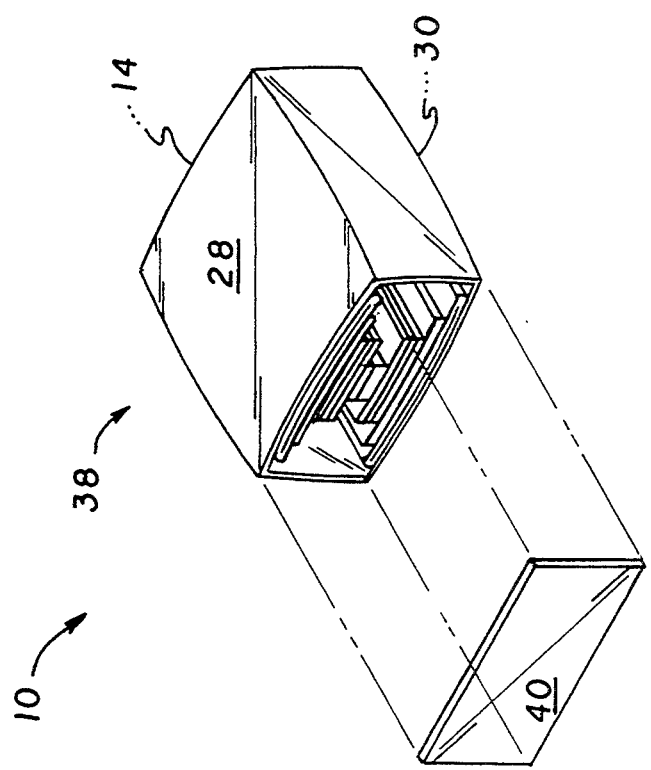
FIG. 4 is a partially exploded, rear perspective view of the baby change kit shown in FIG. 1.

The preferred contents of enclosure 12 allow for two complete diaper changes, and their arrangement inside enclosure 12 is illustrated in FIGS. 3 and 4. Positioned adjacent to opposing surfaces 28,30 of enclosure 12 are first and second diapers 24,25, each folded appropriately to fit into enclosure 12. Each of these diapers 24,25 includes tie straps 26,27 for securing diapers 24,25 in their folded position, which is important to maintain the compactness of diapers 24,25, and also to prevent expansion either diaper 24 or 25 when other supplies are removed from enclosure 12. These tie straps 26,27 are fabricated from polypropylene based plastic, and the ends of each strap 26,27 include adhesive usable for securing each strap 26,27 around its respective diaper 24,25.

In the folded position, diaper 24 includes a first main side 32, and diaper 25 includes a second main side 33. The folding of the diapers 24,25 is such that these sides 32,33 are approximately the same size as surfaces 28,30. The positioning of main sides 32,33 substantially entirely in communication with surfaces 28,30, respectively, results in both of the surfaces 28,30 being substantially uniform and pliable, which facilitates carrying and storage of kit 10, and also assures surfaces 28,30 are capable of receiving printed matter and the like.

Located intermediate diapers 24,25 are two fluid impermeable disposal bags 22,23, two wet wiping elements 20,21, two packages of baby powder 34,35, and two packages of baby cream 36,37. Disposal bags 22,23 are folded to conform to the diminutive size constraints of enclosure 12, and wet wiping elements 20,21 are each covered by a moisture impermeable, transparent wrapping. Each of these wet wiping elements 20,21 contains three independent wiping cloths.

The enclosure includes a main body 38 and a surface or portion 40 attached to main body 38 by a continuous seal, such as a heat seal. Prior to attaching portion 40, the supplies are placed into main body 38 through the opening 42, existing because portion 40 is detached from main body 38. Due to the flexibility of main body 38, it may be beneficial to have an external mechanism holding main body 38 open while the supplies are placed therein. One such mechanism, commonly known to those in the field of manufacturing, is a blower (not shown) for forcing air into main body 38.

Figure 5:
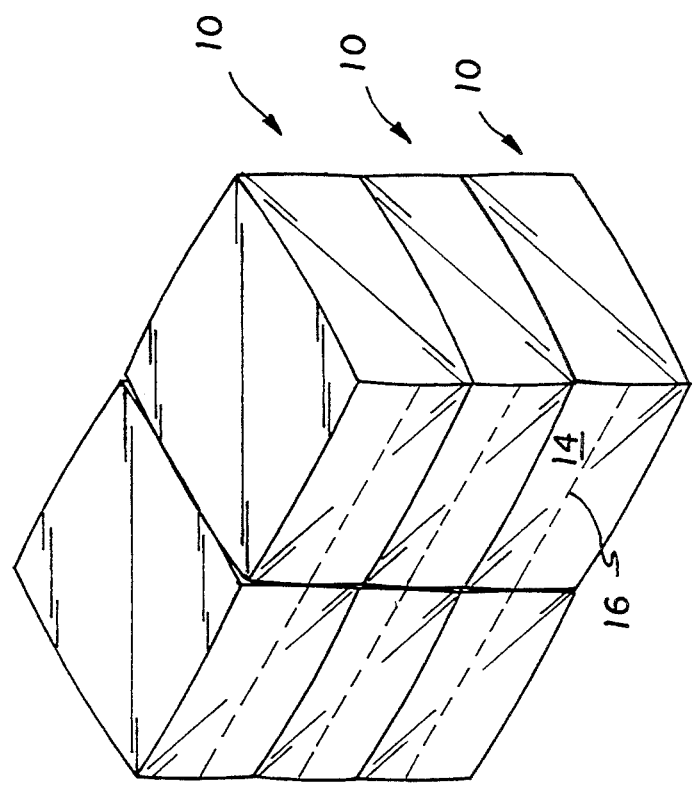
FIG. 5 is a front perspective view of a plurality of baby change kits of the invention.

After the supplies are placed into main body 38, portion 40 is attached to main body 38 to seal enclosure 12 from moisture and dirt particles. The result is a highly compact enclosure 12 that can be stored, transported, or otherwise handled, without concern of contamination of the supplies. In FIG. 5, there is illustrated a plurality of kits 10 stacked upon each other. This stacking may be desirable when a number of kits 10 are bulk retailed.

As seen in FIGS. 3 and 4, tear line 16 is integral with surface 14, which opposes portion 40. This assures the attachment of portion 40 does not interfere with tear line 16, which completely traverses surface 14. Opening 18, therefore, is provided with the largest possible dimensions when tear line 16 is severed.

Another reason for tear line 16 being integral with surface 14 is for accessibility to the supplies within enclosure 12. As diapers 24,25 communicate with sides 28,30, both of which are adjacent to, and extend from, surface 14, the supplies intermediate these diapers 24,25 are each arranged to have an end proximate surface 14. Therefore, severing tear line 16 permits the user to easily access the desired supply or supplies. If one of diapers 24 or 25 were substantially entirely in communication with surface 14, this diaper 24 or 25 would have to be removed to access the other supplies.

Subsequent to changing a baby's diaper, the soiled diaper and the used supplies are placed into one of the disposal bags 22 or 23 for future discarding. The unused supplies remain inside enclosure 12, and may be utilized for the next changing. That certain supplies have been removed from enclosure 12 causes enclosure 12 to loosely surround the remaining supplies. Therefore, the remaining supplies can be arranged so that enclosure 12 can be tied to seal the contents therein.

When it is desired to change the baby a second time, enclosure 12 is untied, and the remaining supplies utilized for the second changing. Soiled diaper 24 or 25 and all of the used supplies are then placed in the remaining disposal bag 22 or 23 for future discarding. Although it is possible to place soiled diaper 24 or 25 and used supplies into enclosure 12 for discarding, disposal bag bags 22,23 are configured to be substantially larger and more accommodating than enclosure 12.

It is to be understood that the present invention is not limited to the sole embodiment described above, but encompasses any and all embodiments within the scope of the following claims.

I claim:

1. A baby change kit comprising:
   a plurality of baby care supplies including a first diaper, a second diaper, a first moisture impermeable disposal bag, a first wet wiping element having a first moisture impermeable wrapping, a second wet wiping element having a second moisture impermeable wrapping;
   a moisture impermeable enclosure containing said plurality of baby care supplies, said moisture impermeable enclosure having a main body and a portion attached to said main body by a continuous seal, said moisture impermeable enclosure also having a tear line;
   said first diaper includes a first main side, and said second diaper includes a second main side, both said first main side and said second main side being substantially entirely in communication with said moisture impermeable enclosure; and
   said moisture impermeable enclosure includes a first pair of opposing surfaces and a second pair of opposing surfaces, said tear line and said continuous seal being integral with different surfaces of said first pair of opposing surfaces, said first main side and said second main side being substantially entirely in communication with different surfaces of said second pair of opposing surfaces.

2. The baby change kit according to claim 1, further comprising a second moisture impermeable disposal bag.

3. The baby change kit according to claim 1, further comprising two packages of baby powder.

4. The baby change kit according to claim 1, further comprising two packages of baby cream.

5. The baby change kit according to claim 1, wherein said first diaper is folded upon itself, and said second diaper is folded upon itself, there being a first tie strap secured around said first diaper, there further being a second tie strap secured around said second diaper.

6. A baby change kit comprising:
   a plurality of baby care supplies including a first diaper with a first main side, a second diaper with a second main side, two moisture impermeable disposal bags, a first wet wiping element having a first moisture impermeable wrapping, a second wet wiping element having a second moisture impermeable wrapping, two packages of baby powder, and two packages of baby cream; and
   a moisture impermeable enclosure containing said plurality of baby care supplies, said moisture impermeable enclosure having a main body and a portion attached to said main body by a continuous seal, said moisture impermeable enclosure also having a tear line,
   said moisture impermeable enclosure including a first pair of opposing surfaces and a second pair of opposing surfaces, each surface of said second pair of opposing surfaces connecting one surface of said first pair of opposing surfaces to the other surface of said first pair of opposing surfaces,
   said tear line and said continuous seal being integral with different surfaces of said first pair of opposing surfaces, said first main side and said second main side being substantially entirely in communication with said second pair of opposing surfaces.

7. The baby change kit according to claim 6, wherein said first diaper is folded upon itself, and said second diaper is folded upon itself, there being a first tie strap secured around said first diaper, there further being a second tie strap secured around said second diaper.

* * * * *